United States Patent [19]

Riede et al.

[11] 4,158,034

[45] Jun. 12, 1979

[54] STERILIZATION METHOD AND APPARATUS FOR DIALYSIS SYSTEM

[75] Inventors: Gerhard Riede, Vellinge; Lars-Åke L. Larsson, Löddeköpinge; Roland J. E. Andersson, Bjarred; Sven A. Jönsson, Staffanstorp, all of Sweden

[73] Assignee: Gambro AB, Lund, Sweden

[21] Appl. No.: 841,898

[22] Filed: Oct. 13, 1977

[30] Foreign Application Priority Data

Oct. 14, 1976 [SE] Sweden ................. 7611388

[51] Int. Cl.$^2$ .................... A61L 1/00; A61L 3/00; B01D 13/00

[52] U.S. Cl. ................... 422/36; 134/22 C; 210/321 A; 422/28; 422/37; 422/292

[58] Field of Search ............ 21/2, 58, 61, 91, 92; 210/22 R, 22 A, 22 C, 22 D, 321 R, 321 A, 321 B; 134/22 R, 22 C, 42; 422/28, 36, 37, 292

[56] References Cited

U.S. PATENT DOCUMENTS

| | | | |
|---|---|---|---|
| 3,406,826 | 10/1968 | Willock | 210/321 B |
| 3,441,136 | 4/1969 | Serfass et al. | 210/321 B |
| 3,474,907 | 10/1969 | Cary et al. | 210/321 B |
| 3,598,727 | 8/1971 | Willock | 210/321 B |
| 3,727,612 | 4/1973 | Sayers et al. | 210/321 B |
| 3,744,636 | 7/1973 | Commarmot | 210/321 B |
| 3,814,249 | 6/1974 | Eaton | 210/321 B |
| 3,844,940 | 10/1974 | Kopf et al. | 210/321 B |
| 3,871,913 | 3/1975 | Shaldon | 134/22 R |
| 3,878,095 | 4/1975 | Frasier et al. | 210/321 B |
| 4,060,485 | 11/1977 | Eaton | 210/321 B |

Primary Examiner—Morris O. Wolk
Assistant Examiner—Bradley Garris
Attorney, Agent, or Firm—Lerner, David, Littenberg & Samuel

[57] ABSTRACT

A method and apparatus for sterilization of a dialysis system. The dialysis system comprises a dialyzer, a receptacle for water and a receptacle for dialysis concentrate, and fluid conducting means for conducting fluids from the receptacles for water and dialysis concentrate to and through the dialyzer. The method includes the steps of terminating the conducting of dialysis concentrate through the fluid conducting means, introducing sterilizing agent into the fluid conducting means at a first point in the fluid conducting means, conducting the sterilizing agent through the fluid conducting means downstream of the first point, and directing a portion of the sterilizing agent from a second point in the fluid conducting means to a third point in the fluid conducting means, the second point being downstream of the first point and the third point being upstream of the first point. The apparatus includes a source of sterilizing agent, means for introducing sterilizing agent into the fluid conducting means at a first point in the fluid conducting means, and fluid return means for conducting a portion of the sterilizing agent from a second point in the fluid conducting means to a third point in the fluid conducting means, the second point being downstream of the first point and the third point being upstream of the first point. With such a method and apparatus, sterilizing agent is conducted substantially throughout the fluid conducting means of the dialysis system.

26 Claims, 1 Drawing Figure

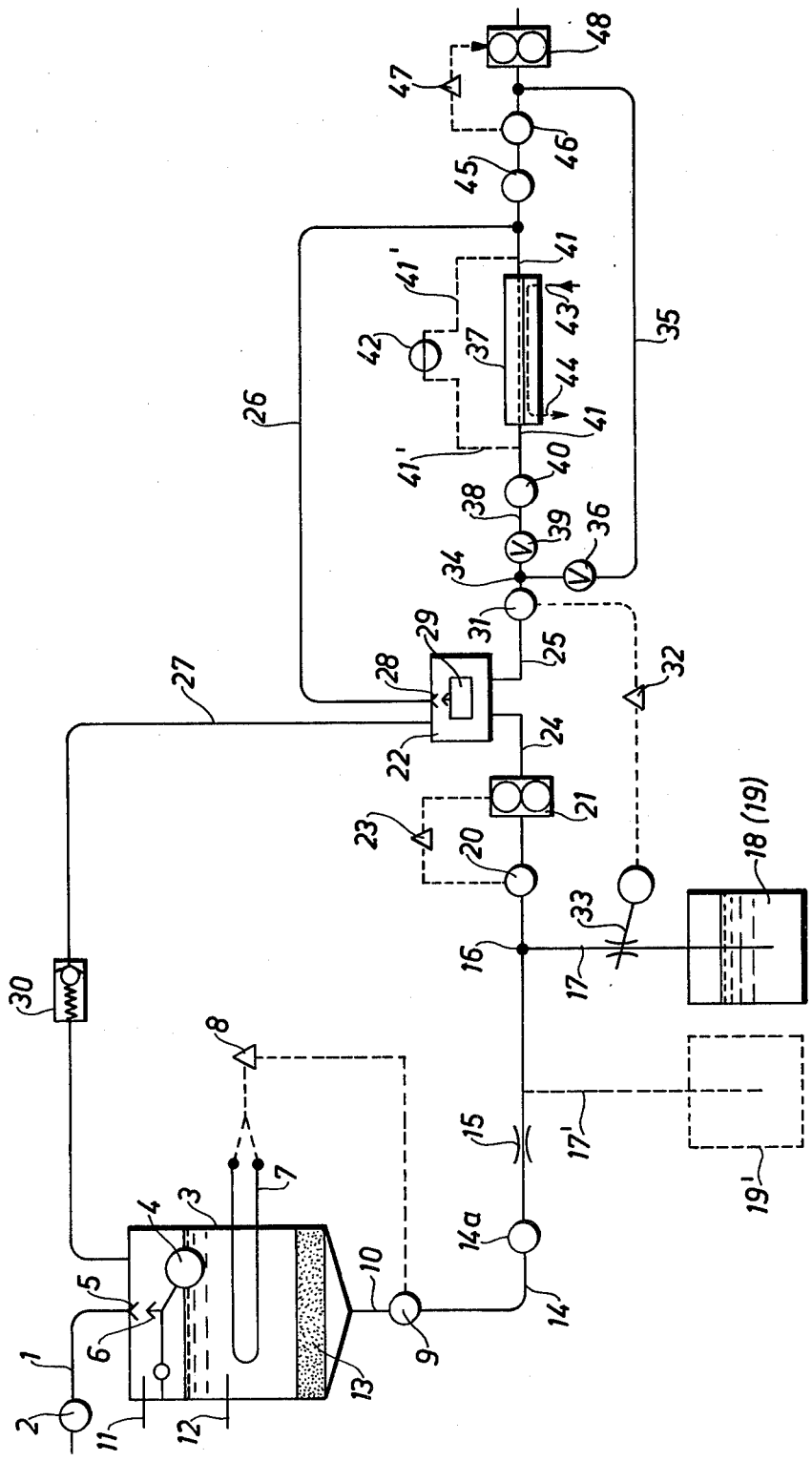

STERILIZATION METHOD AND APPARATUS FOR DIALYSIS SYSTEM

BACKGROUND OF THE INVENTION

The present invention relates generally to dialysis systems, and more particularly to a dialysis system having a dialyzer for treating a first fluid, e.g. blood, with dialysis fluid, a receptacle for water, a receptacle for dialysis concentrate, and means for conducting water and dialysis concentrate from these respective receptacles to and through the dialyzer. Further, means are usually provided for heating the dialysis fluid to a specified desired temperature.

Such dialysis systems usually comprise means for heat sterilization. As a rule, these means consist of the ordinary heating elements which are adapted to heating the water in the water receptacle to a higher sterilization temperature than the normal desired temperature during dialysis. The water is then made to flow through the system in a similar manner to the one in which the dialysis liquid is usually conducted. The only difference is that the tubes or lines which normally are connected to the actual dialyzer are connected instead to a "safety by-pass".

It has long been regarded as desirable, however, to sterilize at lower temperatures. It is an object of the present invention to provide an effective system for "cold sterilization" or "chemical sterilization". For practical reasons this term will be used in the following to cover also disinfection, since the difference between sterilization and disinfection is one of degree rather than of kind. The system may also operate at higher temperatures.

SUMMARY OF THE INVENTION

The sterilization method of the present invention is for a dialysis system which includes a dialyzer, a receptacle for water, a receptacle for dialysis concentrate, and fluid conducting means for conducting fluids from the receptacles of water and dialysis concentrate to and through the dialyzer. The method of sterilization comprises the following steps: first, terminating the introduction of dialysis concentrate into the fluid conducting means; introducing a sterilizing agent into the fluid conducting means at a first point in the fluid conducting means; conducting the introduced sterilizing agent through the fluid conducting means downstream of the first point; and directing a portion of the sterilizing agent from a second point in the fluid conducting means to a third point in the fluid conducting means, the second point being downstream of the first point and the third point being upstream of the first point. In this way, sterilizing agent is conducted substantially throughout the fluid conducting means of the dialysis system.

In the preferred embodiment of the present invention, sterilizing agent is directed from the second point to the receptacle for water and introduced into the water receptacle, and then the mixture of water and sterilizing agent in the receptacle for water is introduced into the fluid conducting means at the third point.

The sterilization apparatus of the present invention is adapted for a dialysis system having a dialyzer, a receptacle for water, a receptacle for dialysis concentrate, and fluid conducting means for conducting fluids from the receptacles of water and dialysis concentrate to and through the dialyzer. The sterilization apparatus includes a source of sterilizing agent, introduction means for introducing sterilizing agent from the source of sterilizing agent into the fluid conducting means of the dialysis system at a first point, and fluid return means adapted to conduct a portion of sterilizing agent from a second point in the fluid conducting means to a third point in the fluid conducting means, the second point being downstream of the first point and the third point being upstream of the first point. In this way sterilizing agent may be pumped substantially throughout the fluid conducting means of the dialysis system.

In a preferred embodiment, the receptacle for water communicates with the fluid conducting means at the third point and the fluid return means is adapted to conduct sterilizing agent from the second point in the fluid conducting means to the receptacle for water. In a still further preferred embodiment, gas removing means, such as a bubble separator, is interposed in the fluid conducting means at the second point, and the fluid return means is adapted to communicate with the gas removing means.

These and other features of the present invention will be described in more detail with reference to the enclosed drawing, which by way of example, describes the preferred embodiment of the sterilization apparatus and method according to the present invention.

BRIEF DESCRIPTION OF THE DRAWING

The single FIGURE is a schematic diagram of the sterilization apparatus of the present invention, together with various elements of the dialysis system with which it is designed to operate.

DETAILED DESCRIPTION OF THE PRESENT INVENTION

Referring to the FIGURE, an inlet line 1 for fresh water leads to a water tank 3 and is provided with an inlet valve 2 for controlling the introduction of water into the tank 3. The water tank 3 is provided with a float valve 4 which is adapted to close the water intake 5 with the help of a shut-off cone 6 when the water tank 3 is full. The water tank 3 moreover comprises means 7 for heating the water, e.g. in the form of a heating coil. This heating coil is controlled in a well known manner by a temperature controller 8 which in turn is responsive to the temperature measured by a temperature transmitter 9 in the outlet line 10 from the tank 3. Furthermore, the tank comprises high and low level controllers shown schematically and marked 11 and 12 respectively for monitoring the liquid level in the tank 3. These level controllers may be adapted for example to control directly the inlet valve 2. Finally, the tank 3 comprises a filter element 13 shown schematically which in the first hand is intended to remove solid particles from the water, but which in practice also removes a certain amount of gas in the water, e.g. free gas bubbles.

After heating, the fresh water delivered to tank 3 is conducted via the outlet line 10, temperature transmitter 9, a line 14 with a shut-off valve 14a and a throttle valve 15 to a branching-off point 16. Here, a branch line 17 is connected which under normal circumstances, i.e. when treatment of a first fluid, e.g. blood, with dialysis fluid is taking place, starts from a source 18 of dialysis concentrate, e.g. a salt solution concentrate. Usually, when the dialysis fluid comprises a salt solution, this source quite simply consists of a keg of concentrated salt solution.

In the sterilization in accordance with the present invention, however, this keg 18 of concentrated salt solution is replaced with a keg or container having sterilizing agent which thus constitutes the source of sterilizing agent and which is designated (19) in the FIGURE. This is the simplest solution in practice since the same supply line 17 is used for both the dialysis concentrate and the sterilizing agent. However, if required for special reasons, it is of course also possible to connect a further line 17' to the system parallel with line 17 for the connection of a separate vessel 19'. This has been indicated in the FIGURE by broken lines. As a sterilizing agent, conventional substances on market may be used, such as for example, formalin or chloramine.

From the point 16 the liquid flows via a pressure pick-up 20 and a pump 21 to a bubble separator 22. The pressure pick-up 20 controls the pump 21 via a pressure controller 23. The feed line to the bubble separator 22 is designated 24. In the embodiment shown in the FIGURE, the pump 21 serves to both draw water and dialysis concentrate from their respective sources, 3 and 18, and to mix the same, in accordance with the invention of copending U.S. Application Ser. No. 841,899, filed on Oct. 13, 1977, the same day as the present application was filed. Also, when sterilization is to take place, the pump 21 will serve to draw sterilizing agent from its receptacle (19) and conduct the same throughout the system.

From the bubble separator 22 there leads firstly an ordinary conducting line 25, secondly a line 26 for the removal of separated gas, and thirdly a fluid return line 27. The inlet 28 to the line 26 is controlled by a float valve 29, which closes this inlet 28 when the bubble separator 22 is filled with liquid, as is the situation to be described hereinbelow in connection with sterilization. The return line 27 is provided with a spring-loaded check valve 30 and leads back to the liquid tank 3.

The line 25 leads to the conductivity meter 31 which via a controller 32 controls variation in the opening of a throttle valve 33 in the line 17 used for introducing dialysis concentrate into line 14. In this way, the amount of dialysis concentrate introduced into the dialysis system, and thus the ultimate concentration of the dialysis fluid which passes through the dialyzer, is controlled. After the conductivity meter 31 the liquid flow reaches a new branching-off point 34 from which departs a shunt line 35 with a valve 36. The shunt line 35 is used in the event a by-passing of the dialyzer 37 by the liquid flow is required quickly, e.g. if a fault is discovered in the dialysis liquid in respect of, for example, the temperature or the salt content. Otherwise, the liquid flows normally to the dialyzer 37 via the line 38 which contains a valve 39 and a flow meter 40. The valve 39 is normally controlled together with the valve 36 for the change-over of the liquid flow. Alternatively, the two valves 36 and 39 can of course be replaced by a three-way valve located at the branching-off point 34.

Numeral 41 designates the lines or tubes which are normally connected to the dialyzer 37. In the event of sterilization, however, these tubes are connected to a "safety-by-pass" 42, which is indicated by broken lines marked 41'. An embodiment of such a "safety-by-pass" is described, by way of example, in U.S. Application Ser. No. 771,257 filed Feb. 23, 1977 now U.S. Pat. No. 4,122,010. It need therefore not be described in detail in conjunction with the present invention. The inlet and outlet of the dialyzer 37 for the fluid, e.g. blood, to be treated with dialysis fluid, are designated 43 and 44 respectively. The dialyzer 37 may take almost any conventional form of dialyzer, such as for example, that described in U.S. Pat. Nos. 3,411,630 and 3,516,548.

Numeral 45 designates a blood detector which gives an alarm and possibly shuts down the whole system if blood is detected in the dialysis fluid exiting from the dialyzer 37. This blood detector 45 may for example, be a transparent tube placed opposite an otherwise screened photocell device which directly monitors the occurence of any blood in the dialysis fluid. After the blood detector 45, the liquid flow passes a pressure gauge 46 which via a controller 47 controls a liquid pump 48. Finally, the liquid flow is passed to a drain, provided no part of the flow is to be recirculated. Such recirculation is well known, however, to those versed in the art and has therefore not been shown in detail in the drawing.

In accordance with the present invention, sterilization of the dialysis system starts with the source of dialysis concentrate 18 being disconnected from the system and replaced with a source of sterilizing agent (19). The pump 21 operates to draw sterilizing agent from the tank or keg (19) into the line 14 and pump 21 to conduct same to the bubble separator 22 via line 24.

Preferably, the return line 27 is adapted to start from a point situated relatively high up in the bubble separator 22, so as to conduct the sterilizing agent from there back into the system at the water tank 3 in which means are normally provided for heating the water. It is appropriate for the return line 27 to start from the highest point of the bubble separator 22 so that the same is always completely filled with sterilizing agent before any is conducted back to the water tank 3. As noted above, a shut-off valve 29 is provided which is adapted to close the line 26, (which normally removes gas given off by the dialysis liquid) when the bubble separator 22 is filled with sterilizing agent.

In the return line 27, the check valve 30 is arranged to prevent flow in the opposite direction, i.e. from the tank 3 to the bubble separator 22. Also, the check valve 30 is preferably spring loaded in order to produce an increase in the pressure so that the sterilizing agent will be conducted under pressure to other points in the system which it otherwise may not reach.

To insure that the whole system is truly sterilized, and to insure that the bubble separator 22 is filled with sterilizing agent, the shut-off valves 36, 39, arranged downstream of the bubble separator 22 may be adapted to be closed when sterilization begins and to only be opened after the part of the system upstream of the bubble separator 22 has been practically all filled with sterilizing agent. Opening and closing of the valves 36, 39, can be accomplished either manually or automatically. Alternatively, assurance that the bubble separator 22 is filled with sterilizing agent can be obtained by operating pump 21 at a greater capacity than pump 48 to insure that more sterilizing agent is introduced by pump 21 into the bubble separator 22 than is withdrawn by pump 48.

Furthermore, if it is desired to have a stronger concentration of sterilizing agent conducted throughout most of the system, the shut-off valve 14a may be closed initially. This would have the effect of preventing dilution of the sterilizing agent by the water in tank 3.

Further, as noted above, during sterilization, sterilizing agent is bypassed around the dialyzer 37 by being conducted through shunt line 35 and/or "safety bypass" 42.

After sterilization, the system in accordance with the present invention normally has to be effectively flushed. This is done appropriately by terminating the flow of sterilization agent from the source (19) and then introducing water via the normal water intake 5. This water is conducted through the different lines of the system up to the liquid pump 48 shown and from there to a drain, and in addition, is conducted, through the lines 10, 14, 24, and 27, back to the liquid tank 3 to flush the entire system of sterilizing agent. In this flushing process it is desirable to flush the entire liquid tank 3. However, owing to the action of the high-level monitor 11, the liquid tank 3 will not completely fill up. Accordingly, it may be expedient to arrange the line 27 in such a manner that the whole of the liquid tank 3 will nevertheless be flushed, such as for example, by making the line 27 open directly above the float 4 so that sterilizing liquid as well as flushing liquid will sprinkle throughout the inside of the tank 3. Alternatively, any type of sprinkler system may be arranged in the tank 3 to provide an effective flushing.

Naturally, the invention is not limited solely to the example described above, but may be modified within the scope of the following claims. Thus, the components forming part of the system may be varied in respect of shape as well as function without exceeding the scope of the invention. Moreover, details which are not necessary for the understanding of the invention, but which to those versed in the art are self-evident parts of a complete dialysis system have not been shown in the drawing.

What is claimed is:

1. A method of sterilizing a dialysis system comprising a dialyzer, a receptacle for dialysis concentrate, a receptacle for water, and fluid conducting means for conducting fluids from said receptacle for water and said receptacle for dialysis concentrate to and through the dialyzer, said fluid conducting means including pump means downstream of said receptacles and upstream of said dialyzer for withdrawing fluid from said receptacles for dialysis concentrate and for water into said fluid conducting means and for pumping fluids through said fluid conducting means, said sterilization method comprising the steps of:
   terminating the conducting of dialysis concentrate through said fluid conducting means;
   providing a source of sterilizing agent, separate from the fluids in said receptacles for water and dialysis concentrate, in fluid communication with said fluid conducting means at a first point in said fluid conducting means, said first point being upstream of said pump means;
   withdrawing sterilizing agent from said source of sterilizing agent with said pump means into said fluid conducting means at said first point;
   conducting the sterilizing agent through said fluid conducting means downstream of said first point;
   directing at least a portion of said sterilizing agent from a second point in said fluid conducting means to a third point in said fluid conducting means, said second point being downstream of said first point and of said pump means, and said third point being upstream of said first point;
   stopping the flow of sterilizing agent beyond a fourth point in said fluid conducting means, said fourth point being downstream of said first and second points and upstream of said dialyzer, so that substantially all of the sterilizing agent is conducted to said third point in said fluid conducting means; and
   then starting flow of sterilizing agent in said fluid conducting means beyond said fourth point after sterilizing agent has been conducted substantially throughout the portion of said fluid conducting means upstream of said fourth point so that sterilizing agent is also conducted substantially throughout the remainder of said flow conducting means downstream of said fourth point.

2. The method of claim 1 wherein the directing step comprises conducting a portion of the sterilizing agent to said receptacle for water, introducing said conducted portion of sterilizing agent into said receptacle for water to form a mixture of water and sterilizing agent and introducing the mixture of water and sterilizing agent into said fluid conducting means at said third point.

3. The method of claim 1 further including the step of diverting the flow of sterilizing agent around the dialyzer so that no sterilizing agent is introduced into the dialyzer.

4. The method of claim 1 in which the dialysis system includes introducing means in fluid communication with said fluid conducting means at said fiirst point and in which said receptacle for dialysis concentrate is in fluid communication with said introducing means, and wherein said step of terminating the conducting of dialysis concentrate includes removing the receptacle for dialysis concentrate from fluid communication with said introducing means, and said step of providing a source of sterilizing agent includes placing said source of sterilizing agent in fluid communication with said introducing means.

5. The method of claim 1 further including the step of flushing the sterilizing agent from said fluid conducting means after the sterilizing agent has been conducted substantially throughout said fluid conducting means.

6. The method of claim 5 wherein said flushing step comprises:
   terminating the introduction of sterilizing agent into said fluid conducting means;
   introducing water into said fluid conducting means;
   conducting the water through said fluid conducting means; and
   directing a portion of the water from said second point in said fluid conducting means to said third point in said fluid conducting means.

7. The method of claim 6 wherein the step of introducing water comprises introducing water into said receptacle for water and introducing the fluid in said receptacle for water at said third point in said fluid conducting means.

8. The method of claim 6 wherein the step of directing a portion of the water comprises conducting a portion of the water from said second point to said receptacle for water, introducing said portion of water conducted to said receptacle for water into said receptacle for water, and introducing the fluid in said receptacle for water at said third point.

9. Sterilization apparatus for a dialysis system including a dialyzer, a receptacle for water, a receptacle for dialysis concentrate, and fluid conducting means for conducting fluids from said receptacle of water and said receptacle for dialysis concentrate to and through the dialyzer, said fluid conducting means including pump means downstream of said receptacles and upstream of said dialyzer for withdrawing fluid from said receptacles into said fluid conducting means and for pumping fluids through said fluid conducting means, said sterilization apparatus comprising:

a source of sterilizing agent separate from the fluids in said receptacles for water and dialysis concentrate;

fluid communication means for providing fluid communication between said source of sterilizing agent and said fluid conducting means at a first point in said fluid conducting means, said first point being upstream of said pump means; and fluid return means adapted to conduct at least a portion of sterilizing agent from a second point in said fluid conducting means to a third point in said fluid conducting means, said second point being downstream of said first point and of said pump means, and upstream of said dialyzer, and said third point being upstream of said first point so that said pump means conducts sterilizing agent substantially throughout said fluid conducting means.

10. The apparatus of claim 9 wherein said fluid return means includes one-way flow means, said one-way flow means permitting flow of fluid through said fluid return means only from said second point to said third point and preventing flow of fluid through said fluid return means from said third point to said second point.

11. The apparatus of claim 10 wherein said one-way flow means comprises a spring loaded check valve.

12. The apparatus of claim 9 wherein said fluid return means includes a fluid line for conducting a portion of the sterilizing agent from said second point to said receptacle for water, and wherein said receptacle for water communicates with said fluid conducting means at said third point.

13. The apparatus of claim 12 further including spray means associated with said fluid line for spraying fluid in said fluid line into said receptacle for water.

14. The apparatus of claim 12 wherein the dialysis system further includes gas removing means for removing gas bubbles from fluids, said gas removing means being interposed in said fluid conducting means at said second point, and wherein said fluid line is connected at one end to said gas removing means and at the other end to said receptacle for water so that sterilizing agent is conducted from said gas removing means into said receptacle for water, and from there into said fluid conducting means at said third point.

15. The apparatus of claim 14 wherein said gas removing means comprises a bubble separator and wherein said fluid line is connected to said bubble separator at a position near the top of said bubble separator so that said bubble separator is substantially filled with sterilizing agent before sterilizing agent is conducted from said bubble separator through said fluid line to said receptacle for water.

16. A dialysis system for treatment of a first fluid with dialysis fluid, the system comprising:

a dialyzer in which the treatment occurs;

a receptacle for water;

a receptacle for dialysis concentrate;

fluid conducting means including pump means downstream of said receptacles and upstream of said dialyzer for conducting fluids from said receptacle for water and said receptacle for dialysis concentrate to and through said dialyzer; and sterilization means for sterilizing said system, said sterilization means comprising:

a source of sterilizing agent;

fluid communication means for said source of sterilizing agent, said fluid communication means providing fluid communication between said source of sterilizing agent and said fluid conducting means at a first point in said fluid conducting means, said first point being upstream of said pump means; and fluid return means for conducting a portion of the sterilizing agent from a second point in said fluid conducting means to a third point in said fluid conducting means, said fluid return means communicating with said fluid conducting means at said second point and at said third point, and said second point being downstream of said first point and of said pump means, and upstream of said dialyzer, and said third point being upstream of said first point so that sterilizing agent is conducted substantially throughout said fluid conducting means.

17. The system of claim 16, further including means for terminating the introduction of dialysis concentrate from said receptacle for dialysis concentrate into said fluid conducting means.

18. The system of claim 16 further including shut-off means disposed at a fourth point in said fluid conducting means, said fourth point being upstream of said first point and downstream of said third point, for stopping the flow of fluids through said shut-off means.

19. The system of claim 16 further including shut-off means having open and closed positions, said shut-off means being disposed at a fourth point in said fluid conducting means and said fourth point being downstream of said second point, said shut-off means when in said closed position stopping the flow of fluids at said fourth point in said fluid conducting means so that substantially all of the sterilizing agent is conducted to said third point in said fluid conducting means when closed, and said shut-off means when in said open position permitting flow of fluid downstream of said fourth point.

20. The system of claim 16 further including by-pass means for by-passing sterilizing agent in said fluid conducting means around said dialyzer, said by-pass means including a shunt line communicating with said fluid conducting means at a point upstream of said dialyzer and at a point downstream of said dialyzer, and diverting means for diverting fluid in said fluid conducting means into said shunt line.

21. The system of claim 16 wherein said fluid return means includes one-way flow means, said one-way flow means permitting flow of fluid through said fluid return means only from said second point to said third point and preventing flow of fluid through said fluid return means from said third point to said second point.

22. The system of claim 21 wherein said one-way flow means comprises a spring loaded check valve.

23. The system of claim 16 further including gas removing means for removing gas bubbles, said gas removing means being interposed in said fluid conducting means at said second point, and wherein said fluid return means includes a fluid line communicating with said gas removing means at one end and said receptacle for water at the other end, and wherein said receptacle for water communicates with said fluid conducting means at said third point.

24. The system of claim 23 further including spray means associated with said fluid line for spraying fluid in said fluid line into said receptacle for water.

25. The system of claim 23 wherein said gas removing means comprises a bubble separator and wherein said fluid line communicates with said bubble separator at a position near the top of said bubble separator so that said bubble separator is substantially filled with sterilizing agent before sterilizing agent is conducted from said bubble separator through said fluid line to said receptacle for water.

26. The system of claim 25 in which said bubble separator further includes an opening in the top thereof, through which gas bubbles in said bubble separator are removed, and shut-off means for closing said opening when said bubble separator is filled with sterilizing agent.

* * * * *